(12) United States Patent
Mosler et al.

(10) Patent No.: US 10,292,841 B2
(45) Date of Patent: May 21, 2019

(54) DEVICE WITH A WALL DESIGNED TO TIGHTLY ENCLOSE A BODY PART

(75) Inventors: Lüder Mosler, Duderstadt (DE); Bernhard Graimann, Obernfeld (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 0 days.

(21) Appl. No.: 14/233,624

(22) PCT Filed: Mar. 23, 2012

(86) PCT No.: PCT/EP2012/001281
§ 371 (c)(1),
(2), (4) Date: Jan. 17, 2014

(87) PCT Pub. No.: WO2013/010597
PCT Pub. Date: Jan. 24, 2013

(65) Prior Publication Data
US 2014/0188251 A1    Jul. 3, 2014

(30) Foreign Application Priority Data

Jul. 20, 2011    (DE) .......................... 10 2011 108 136

(51) Int. Cl.
*A61F 2/72*  (2006.01)
*A61F 2/78*  (2006.01)
(Continued)

(52) U.S. Cl.
CPC .............. *A61F 2/7812* (2013.01); *A61F 2/72* (2013.01); *A61N 1/0452* (2013.01);
(Continued)

(58) Field of Classification Search
CPC ....................................................... A61F 2/72
(Continued)

(56) References Cited

U.S. PATENT DOCUMENTS 4,708,716 A * 11/1987 Sibalis .................. A61M 37/00
424/449
5,341,813 A    8/1994 Teare et al.
(Continued)

FOREIGN PATENT DOCUMENTS

DE    102005021412 A1    11/2006
DE    202006007460 U1    10/2007
(Continued)

OTHER PUBLICATIONS

Collins, Scientific American, Aug. 2004: pp. 74-81.*
(Continued)

*Primary Examiner* — David H Willse
(74) *Attorney, Agent, or Firm* — Holland & Hart, LLP

(57) ABSTRACT

A device with a wall (6) designed to tightly enclose a body part is made of an electrically non-conductive material (9) and has a shape adapted to the body part or adapting thereto as a result of the elasticity of the wall, wherein an inner face (7) of the wall (6) comes to bear on the skin (14) of the body part, and the inner face (7) is provided with at least one electrically conductive portion (4) which, in order to transmit electrical signals from or to the skin (14) of the body part, is arranged all the way through the electrically non-conductive material (9) of the wall (6), permits reliable transmission of electrical signals with a simple design of the liner, by virtue of the fact the electrically conductive portion (4) is covered by the electrically non-conductive material (9) and is connected to at least one conductor (5, 5') passing through the electrically non-conductive material (9).

26 Claims, 5 Drawing Sheets

(51) Int. Cl.
*A61N 1/04* (2006.01)
*A61N 1/36* (2006.01)
*A61F 2/68* (2006.01)
*A61F 2/50* (2006.01)

(52) U.S. Cl.
CPC .. *A61N 1/36003* (2013.01); *A61F 2002/5056* (2013.01); *A61F 2002/6827* (2013.01); *A61F 2002/7818* (2013.01)

(58) Field of Classification Search
USPC .......................................................... 623/25
See application file for complete search history.

(56) References Cited

U.S. PATENT DOCUMENTS

| | | | |
|---|---|---|---|
| 5,443,525 A | | 8/1995 | Laghi |
| 5,571,208 A | | 11/1996 | Caspers |
| 7,670,385 B2 | | 3/2010 | Klein |
| 8,591,599 B1 * | | 11/2013 | Kaliki et al. ......... A61B 5/6828 |
| | | | 600/372 |
| 8,945,236 B2 | | 2/2015 | Leiniger et al. |
| 9,180,027 B2 | | 11/2015 | Kettwig et al. |
| 2006/0089725 A1 * | | 4/2006 | Kurth ....................... A61F 2/80 |
| | | | 623/36 |
| 2007/0021841 A1 * | | 1/2007 | Al-Temen ................ A61F 2/54 |
| | | | 623/25 |
| 2007/0265711 A1 | | 11/2007 | Klein |
| 2009/0216339 A1 | | 8/2009 | Hanson et al. |
| 2010/0030341 A1 | | 2/2010 | Dietl et al. |
| 2010/0036455 A1 * | | 2/2010 | Sanders ............... A61B 5/0535 |
| | | | 607/48 |
| 2010/0114238 A1 * | | 5/2010 | Muccio .......................... 607/46 |
| 2010/0318195 A1 * | | 12/2010 | Kettwig et al. ................ 623/36 |
| 2012/0296444 A1 * | | 11/2012 | Greenberg et al. ............. 623/25 |
| 2012/0296445 A1 | | 11/2012 | Leiniger et al. |

FOREIGN PATENT DOCUMENTS

| | | | | |
|---|---|---|---|---|
| DE | 102007035409 A1 | 1/2009 | | |
| DE | 202010005472 U1 | 9/2010 | | |
| DE | 102010005462 A1 | 7/2011 | | |
| JP | 2011-125677 A * | 6/2011 | ............... | A61F 2/48 |
| RU | 90983 U1 | 1/2010 | | |
| WO | WO 99/24109 A2 * | 5/1999 | ............... | A61N 1/00 |

OTHER PUBLICATIONS

English language translation of WO 99/24109 (published May 20, 1999): description and claims.*
PCT International Search Report for PCT International Patent Application No. PCT/EP2012/001281, dated Jul. 3, 2012.

* cited by examiner

DEVICE WITH A WALL DESIGNED TO TIGHTLY ENCLOSE A BODY PART

TECHNICAL FIELD

The invention relates to a device having a wall, which is designed to tightly enclose a body part, comprises an electrically nonconductive material and has a shape which is adapted to the body part or adapts thereto by virtue of the elasticity of the wall, wherein the wall comes to bear on the skin of the body part via an inner face and the inner face is provided with at least one electrically conductive section, which is arranged in order to transmit electrical signals from or to the skin of the body part through the electrically nonconductive material of the wall.

BACKGROUND

Devices of the type discussed here are bandages wound tightly around the body part, or liners which are pulled over an amputation stump. The liners have a certain wall thickness and have the function of forming a padding interlayer, adapting or adapted to the amputation stump, between the amputation stump and the inner face of a prosthesis shaft. The prosthesis shaft is part of a prosthesis which replaces the amputated part of an extremity of the patient.

The transmission of electrical signals between the amputation stump and the outer side of the liner may be envisioned for many reasons. For instance, it may be expedient to transmit electrical signals from the skin of the amputation stump outward, in order to control the function of the prosthesis. In this case, the electrodes may be myoelectrical electrodes which pick up muscle contraction signals at suitable points on the amputation stump, so that it is possible to control corresponding prosthetic limbs. Myoelectrical control of prostheses is known in particular for arm and hand prostheses, but may also be used for leg and foot prostheses.

It may furthermore be expedient to electrically determine the surface resistance of the skin of the amputation stump by measuring a flow of current between two or more electrodes, or electrode sections. In this way, for example, it is possible to determine whether the skin of the amputation stump inside the liner is perspiring, which may impair the purchase of the liner on the amputation stump—and therefore the purchase of the prosthesis. It is furthermore possible to determine the application pressure of the amputation stump on the inner face of the liner using electrodes, for example so as to be able to respond to a decrease in the mass of the amputation stump while the prosthesis is being worn.

On the other hand, it may be expedient to transmit electrical signals from the outer side of the liner onto the skin of the amputation stump, for example in order to stimulate a muscle contraction of the amputation stump when the wearer of the prosthesis is in a passive, for example seated, position for a prolonged period of time.

A liner which is provided for accommodating myoelectrical electrodes is known by U.S. Pat. No. 5,443,525. To this end, a nonmetallic, flexible and soft flat pad, in which there are a large number of discrete conductive electrodes, is adhesively bonded into a window of the prosthesis shaft. The liner preferably consists of silicone, a nonconductive flexible synthetic material. The electrodes may be formed from a mixture of silicone and carbon or of silicone and silver, the electrodes respectively being surrounded by nonconductive silicone. The electrode arrangement is therefore adhesively bonded by means of the pad onto the inner side of the liner, and is accessible through the window of the liner so that the myoelectrical signals picked up by the electrodes can be fed outward through the window for evaluation and control. This arrangement is elaborate to produce and has limited wearing comfort. Furthermore, the window of the liner requires particular sealing outlay when the liner—as is often usual—must be airtight in order to hold the liner on the amputation stump with the aid of a reduced pressure formed inside the liner. The reduced pressure must in this case be maintained by the liner against the weight of the moving prosthesis.

US 2009/0216339 A1 discloses a similar liner, in which a conductive insert provided for connection to an electrode is fitted into a corresponding opening of the liner and bears on the outer side of the liner at the edge of the opening with a flange-like edge. The insert is adhesively bonded to the liner. The height of the insert may be selected in such a way that it corresponds to the thickness of the liner. Primarily, however, the intention is that the insert protrudes inward beyond the inner face of the liner in order to press against the tissue of the amputation stump. On the inner side of the liner, an air gap or a gap filled with adhesive is formed between the insert and the wall of the liner. The disadvantages mentioned above also apply for this design, namely increased outlay for the production of airtightness of the adhesive bond, which may be exposed to high mechanical stresses. With high production outlay, therefore, functional reliability is not fully ensured.

This problem also arises in the solution according to DE 20 2006 007 460 U1, in which a special holder for conductive electrode sections, which bears with a flange-like edge on the inner side of the liner, is provided.

DE 10 2010 005 462 A1, not yet published at the priority date of the present application, describes a liner in which a conductive section is integrated into the material of the liner and forms a unitary, continuously aligned inner face with the nonconductive material of the liner. The nonconductive material of the liner is preferably a polymer, in which case the conductive section may be inserted into the material before polymerization of the nonconductive material so that the conductive section is connected to the material of the liner during polymerization thereof to form a unitary part, and the smooth continuous inner face is formed. The conductive section may in this case also consist of the per se nonconductive material of the liner, which has been made electrically conductive with additives. The conductive section may be polymerized together with the material of the liner. The conductive section is in this case used for electrical connection of the skin surface of the amputation stump to a separate electrode, which is arranged directly on the other side of the conductive section and picks up electrical signals, for example myoelectrical signals, from the skin of the amputation stump, or alternatively generates excitation signals which are transmitted via the conductive section onto the skin. To this end, the liner has for example a reception chamber on the outer side of the electrically conductive section, into which an electrode can be mechanically inserted. The shaping which this requires for the liner entails additional outlay.

The problems arising with liners for an amputation stump also exist in a similar form for bandages which are wound around a body part, for example around an extremity, around the trunk of the body, or the like.

SUMMARY

The object of the present invention is to refine a device of the type mentioned in the introduction, in such a way that with a simple structure it is suitable for the transmission of electrical signals.

In order to achieve this object, a device of the type mentioned in the introduction is characterized according to the invention in that the electrically conductive section is covered by the electrically nonconductive material and is connected to at least one conductor passing through the electrically nonconductive material.

The device according to the invention therefore provides an electrically conductive section, with which the electrically conductive signal can be transmitted from or onto the skin of the body part, without the device having to be provided with particular shaping at this position. Rather, the electrically conductive section is covered by the electrically nonconductive material so that the electrically conductive section only remains uncovered toward the inner face and—with the exception of the inner face—is surrounded on all sides by nonconductive material. The electrically conductive section is connected to a conductor, which is passed through the electrically nonconductive material and thus delivers the electrical signal to a position of the device where the connection to a measurement or evaluation device or to an excitation current generator can be established without problems. The conductor is in this case formed as a narrow elongate element, which is preferably arranged in an axial direction of the liner. The axial direction is perpendicular to the circumferential direction of the tubular or funnel-shaped liner, which may be formed so that it is open or closed at its distal end. A closed configuration of the liner at the distal end is preferred.

The conductor may be formed integrally with the electrically conductive section, that is to say consisting of the same material as the electrically conductive section and preferably having been produced together therewith.

In a preferred embodiment of the invention, the conductive section is integrated into the nonconductive material of the wall and forms a unitary and continuously formed inner face with the nonconductive material of the wall.

The electrically conductive section may, however, also be connected to a separate conductor laid in the nonconductive material, which may then consist of a different material, for example metal.

The device according to the invention is formed in order to forward the electrical signals through the wall at a suitable position on the outer side of the wall, where contact with a signal processing unit or a signal generator can readily be established, for example inside the structure of a prosthesis or orthesis. In the case of a measurement signal, this signal is therefore transmitted unevaluated. Particularly in the case of measurement signals, a problem may then arise with respect to the signal-to-noise ratio.

In a particularly preferred embodiment of the invention, an amplifier circuit, which is covered by the nonconductive material of the wall and is connected by at least one terminal to the conductive section, is arranged directly on the conductive section. At least one other terminal of the amplifier circuit is connected to the at least one conductor.

An electrical measurement signal picked up by the electrically conductive section from the skin of the body part can therefore be preamplified directly at the electrically conductive section, so that it can be transmitted as a—moreover still unprocessed—electrical signal with an improved signal-to-noise ratio via the conductor. The amplifier circuit is in this case formed as an integrated circuit and is arranged directly on the electrically conductive section, in such a way that a terminal of the amplifier circuit has electrical contact with the electrically conductive section in order to establish an electrical connection between the terminal and the electrically conductive section. The amplifier circuit is connected by another terminal to the conductor. This terminal may for example be used for supply of electrical current, in which case the connection may be established to an electrical voltage source or an electrical current source, depending on the application. In such an arrangement, the electrical signal may, for example, be transmitted as a measurement signal wirelessly to a receiver. As an alternative, it is possible for the amplifier circuit terminal carrying the amplified measurement signal to be connected to the conductor, so as to transmit a preamplified measurement signal via the conductor to an evaluation circuit. Although wireless electricity supply is also possible, for example inductively, in this embodiment it is advantageous to provide a second conductor for the supply of electrical energy, which is then connected to the corresponding terminal of the amplifier circuit.

In order not to require two conductors laid in the nonconductive material of the wall in order to deliver a supply voltage, the wall may have an electrically conductive layer which is arranged insulated from the electrically conductive section and is formed so that it can be connected to a terminal of the electricity supply. Preferably, a ground terminal or a neutral conductor of the voltage supply is connected to this electrically conductive layer of the wall, which may lie on the outer side or on the inner side of the nonconductive material of the wall. In this case, an electrical connection to a corresponding terminal of the amplifier circuit may be established. The conductive layer located on the outer side furthermore safeguards the signal line against incidence of interference signals.

If the conductive layer lies on the inner side of the wall, so that it forms a part of the inner face, surrounding insulation must naturally be ensured in the region of the electrically conductive section so that a measurement signal or excitation signal relative to the ground potential can be transmitted and is not directly dissipated to ground. This ensures that the skin surface of the body part outside the measurement point is at a defined electrical potential, which is determined by the electrically conductive wall layer connected to this potential.

The amplifier circuit preferably has at least one transistor, in particular a field-effect transistor, and is preferably formed by a transistor, in particular a field-effect transistor with its terminals. The field-effect transistor may in this case be connected in conventional amplifier configurations, for example so as to bring about voltage amplification or current amplification, depending on the application.

By use of the amplifier circuit, for example to preamplify a measurement signal or for impedance conversion, a substantial improvement of signal derivation is achieved without particular wiring outlay being required for this.

A single conductive section of a device has been described above. For the person skilled in the art, it is clear that, particularly for picking up myoelectrical signals, a device, in particular a liner, having a plurality of conductive sections should be provided. Furthermore, it is also possible to implement the arrangement according to the invention for a device, in particular a liner, which has a plurality of conductive sections in particular regions, for example in order to pick up or apply a measurement or excitation signal at a relevant position of the body part. In this way, it is possible to compensate tolerances in the positioning of the device on the body part, because the relevant position of the body part merely has to lie in a particular region and need not necessarily coincide with an individual conductive section.

In a preferred embodiment, the nonconductive material of the wall is a hydrophobic material. As an alternative or in addition thereto, the conductive section consists of a hydrophilic material. In this case, the two features may also be achieved by providing a material with a hydrophobic or hydrophilic coating. In this case, the nonconductive material of the wall is provided with a hydrophobic coating. The conductive section may be provided with a hydrophilic coating.

In order to establish the best possible electrical contact between the skin of the wearer of the device and the conductive section, it is advantageous for there to be a film of moisture between them, or for the conductive section to be moistened. This can be achieved straightforwardly with a hydrophilic material, i.e. one which attracts water. If the rest of the inner face of the device is in addition made from a hydrophobic material, or provided with a hydrophobic coating, this region remains dry owing to the water-repellent effect of the material. This leads to an improved skin compatibility in the applied state.

In particular, the effect achieved by the hydrophobic and hydrophilic properties of the corresponding areas of the inner side of the liner is that there is at least almost no residual liquid on the hydrophobic parts, so that the risk of short circuits and unintended transmissions of electrical signals is reduced or even entirely eliminated. This makes cleaner signal transmission possible.

Naturally, it is possible to use active and passive electrodes, that is to say ones with an integrated or separate amplifier element.

A corresponding device can be cleaned and fitted particularly straightforwardly. For example, it is possible first to wet the inner face of the device with water, for example to fill the device with water. The water is subsequently removed from the device. This is done, for example, by tipping the water out of the device. The hydrophobic, water-repellent material of the inner wall is in this case almost entirely dry, so that a comfortable wearing sensation and hygienic use are achieved here. The hydrophilic, water-attracting material of the conducting region, on the other hand, remains moistened and thus ensures good electrical contact.

The hydrophobicity of materials and their surfaces can, for example, be specified by the contact angle. The greater the contact angle is, the more hydrophobic the surface is. In this context, surfaces with a contact angle of less than 90° are referred to as hydrophilic and surfaces with a contact angle of more than 90° are referred to as hydrophobic.

BRIEF DESCRIPTIOON OF DRAWINGS

The invention will be explained in more detail below with the aid of exemplary embodiments represented in the drawings, in which.

DETAILED DESCRIPTION

Figure 1:
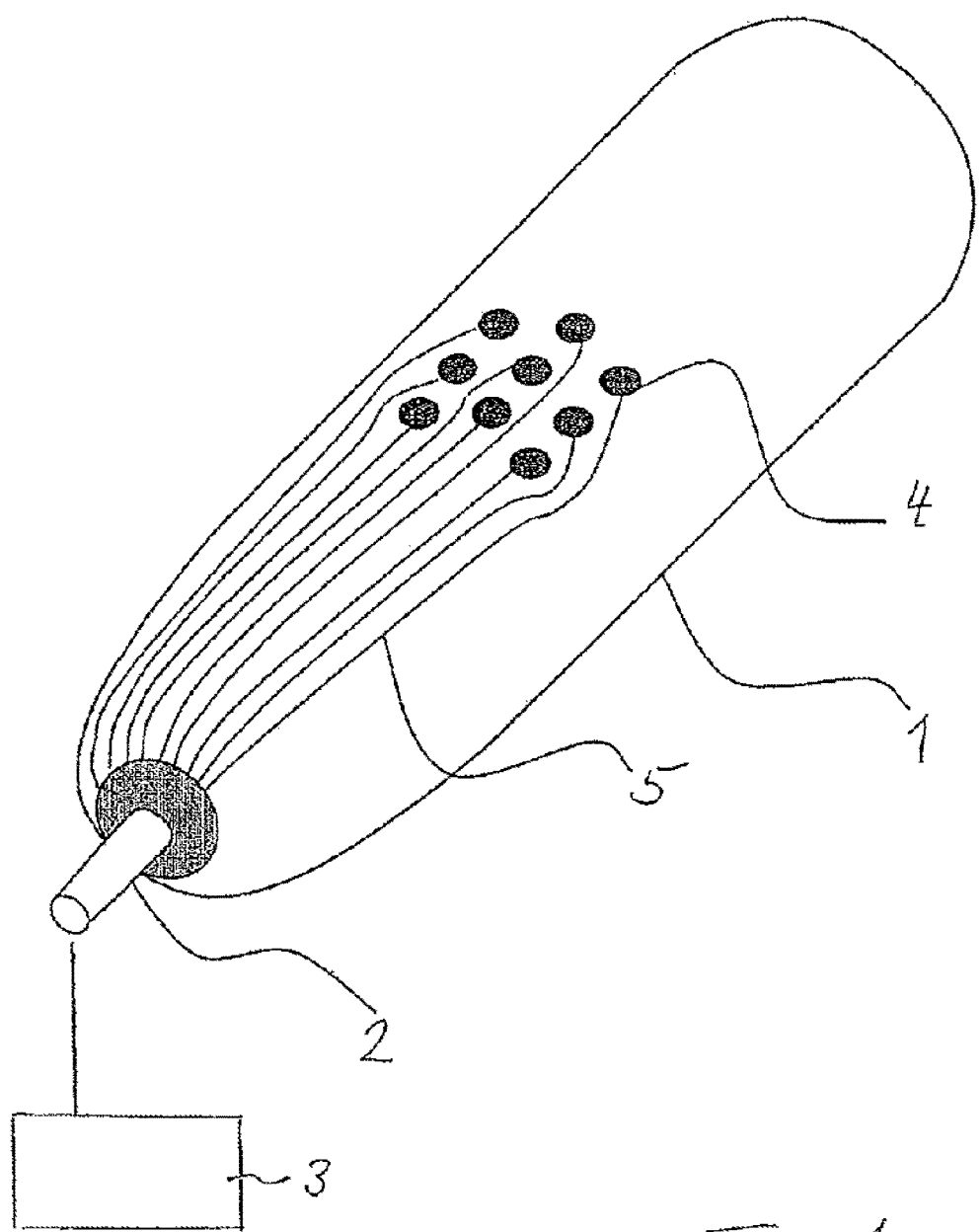
FIG. 1 shows a schematic representation of a liner having a plurality of electrically conductive sections, which are connected via conductors to a multi-pole plug at the distal end of the liner so that a connection to an evaluation or control circuit is established.

FIG. 1 shows, as an example of a device according to the invention, a schematic representation of a liner 1 such as may be used for a leg or arm prosthesis. The liner 1 is designed to be pulled over an amputation stump, and has a hollow interior. In adaptation to the amputation stump, the sleeve-like liner may slightly taper conically toward the distal end. In the exemplary embodiment represented, the liner 1 is closed at the distal end and is formed here with a plug appendage 2 by which the liner can be connected mechanically to a prosthesis. At the same time, the plug appendage 2 is used as an electrical connection means for an evaluation or control circuit 3. The liner is used for padding the amputation stump with respect to a prosthesis shaft (not represented), by which the prosthesis is fastened on the amputation stump. In order to improve the purchase in the prosthesis shaft, a reduced pressure, by which the respective adhesion is improved, may be applied between the prosthesis shaft and the liner 1 and/or between the liner 1 and the amputation stump.

FIG. 1 schematically represents that the wall of the liner 1 is provided in one region with a plurality of electrically conductive sections 4, which are respectively connected via a conductor 5 to the plug appendage 2.

For reasons of clarity, only one region comprising electrically conductive sections 4 is represented. It is to be understood that the liner may also have a plurality of regions comprising electrically conductive sections 4. For accurately positionable liners 1, it is furthermore conceivable for the liner to have only one electrically conductive section 4, or only one electrically conductive section 4 in each region of interest.

Figure 2:
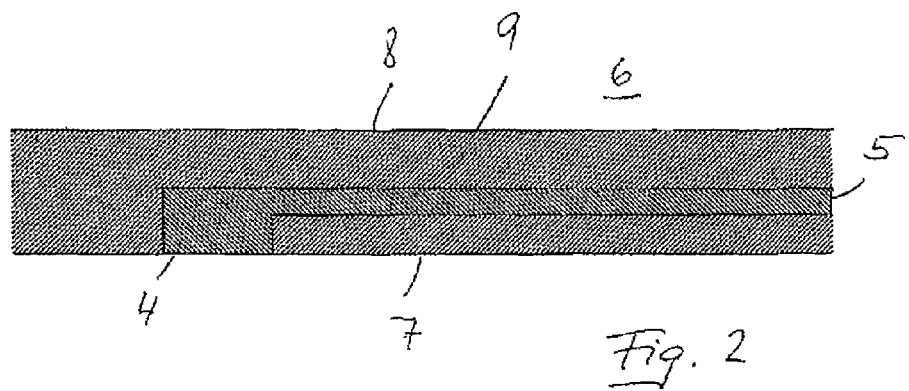
FIG. 2 shows a representation according to FIG. 1 for an embodiment in which the electrically conductive section is connected to a separate conductor.

FIG. 2 shows a first exemplary embodiment of a wall 6 of the liner 1, which has an inner face 7 and an outer side 8. The wall 6 consists of a unitary nonconductive material 9, which therefore forms the inner face 7 and the outer side 8. On the inner face 7, the electrically nonconductive material 9 is interrupted by an electrically conductive section 4, which in the exemplary embodiment represented forms the unitary and continuously formed inner face 7 into the nonconductive material. In the exemplary embodiment represented, the electrically conductive section 4—with the exception of the inner face 7—is surrounded on all sides by the electrically nonconductive material 9. It is formed integrally with the conductor 5 laid inside the nonconductive material 9, so that electrical signals can be fed via the electrically conductive section 4 and the conductor 5, for example onto the distal end of the liner 1 to a plug appendage 2, as can be seen in the exemplary embodiment represented in FIG. 1.

Figure 3:
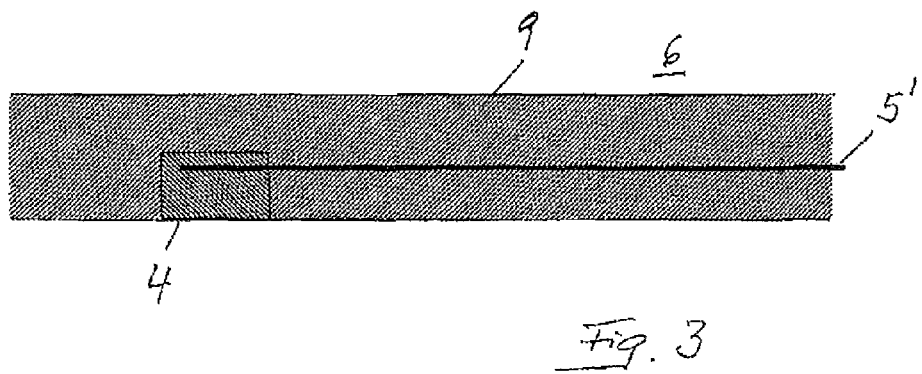
FIG. 3 shows a representation according to FIG. 2, in which an amplifier circuit, which is connected to the conductor, is arranged on the electrically conductive section.

In the exemplary embodiment represented in FIG. 3, the electrically conductive section 4 is connected to a separate conductor 5', which extends through the electrically nonconductive material 9 of the wall 6, for example likewise to a distal end of the liner 1. The conductor 5' may in this case be formed as a metal conductor, for example conductor wire, which is introduced during production of the wall 6 of the liner 1, for example by casting into the wall 6 by placement into a corresponding casting mold. The connection of the conductor 5' to the electrically conductive section 4, configured as a block, may for example be carried out in the not yet polymerized state of the electrically conductive section. The electrically conductive section, preferably formed by a polymer material, may in this case be polymerized before or simultaneously with the electrically nonconductive material 9 of the wall.

Figure 4:
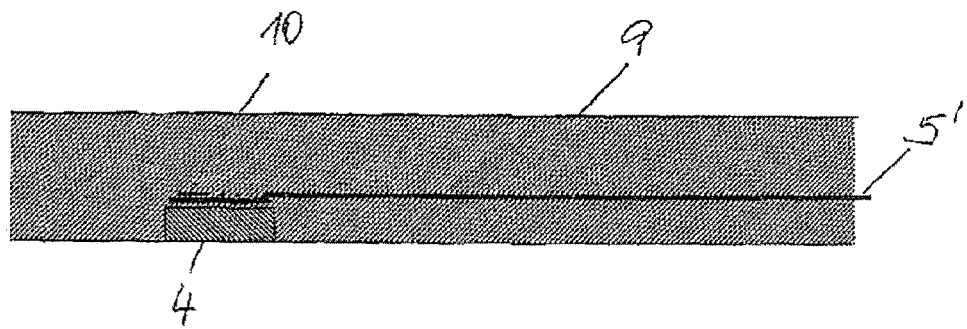
FIG. 4 shows a representation according to FIG. 3, in which the amplifier circuit is connected by a further terminal to an electrically conductive layer on the outer side of the liner.

A preferred nonconductive material 9 of the wall 6 is silicone or polyurethane. FIG. 4 illustrates that an amplifier circuit, by which the electrical signals picked up by the electrically conductive section 4 can be preamplified before they are delivered via the conductor 5', for example to the plug appendage 2, is applied onto the electrically conductive section 4. Here again, the electrically conductive section 4—together with the amplifier circuit—is surrounded on all sides—with the exception of the inner face 7—by the nonconductive material 9.

Figure 5:
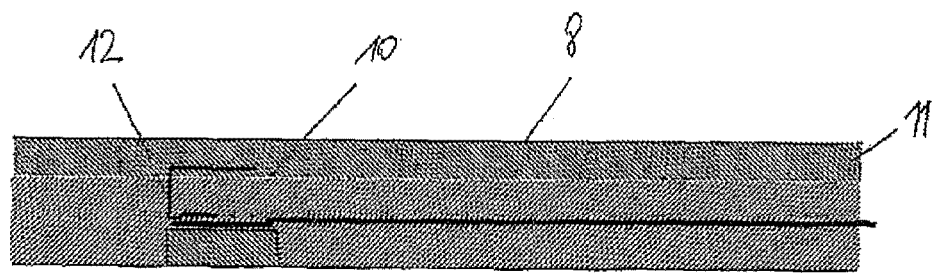
FIG. 5 shows an arrangement according to FIG. 3, in which an electrically conductive layer is arranged on the inner side of the wall, but insulated from the electrically conductive section, and a terminal of the amplifier circuit is connected to this layer.

In the exemplary embodiment represented in FIG. 5, the wall is provided surface-wide with a conductive layer 11 on the outer side 8. This conductive layer is expediently connected to a terminal of a voltage source. With the aid of the conductive layer 11, a connection 12 of the conductive layer 11 to a terminal of the amplifier circuit can therefore be established in a straightforward way, as illustrated in FIG. 5.

Figure 6:
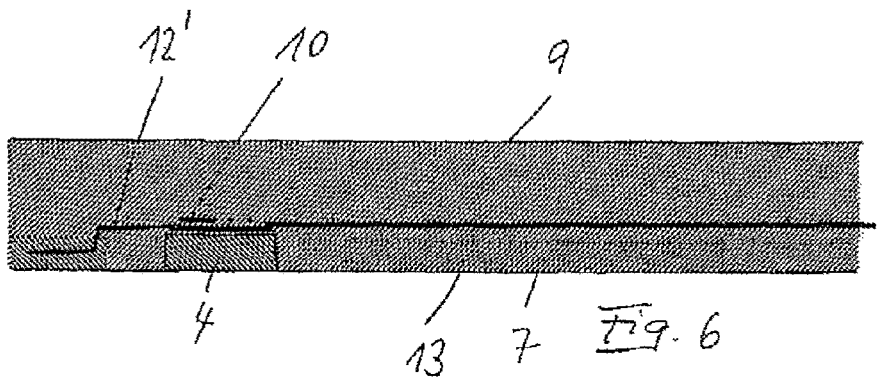
FIG. 6 shows a representation of a wall of the liner, which consists predominantly of a conductive material, the conductive section being covered by an electrically nonconductive material and the liner connected to the amplifier circuit being laid inside nonconductive material.

In the variant represented in FIG. 6, there is a conductive layer 13 on the inner side of the nonconductive material 9, so that the conductive layer 13 predominantly forms the inner face 7 of the liner. The conductive layer 13 forms a flush inner face 7 with the conductive section 4, the nonconductive material 9 being arranged between the conductive layer 13 the electrically conductive section 4 toward the inner face 7, so that the electrically conductive section 4 is in turn surrounded by nonconductive material 9 on all sides—except for the inner face 7. In this exemplary embodiment as well, a terminal of the amplifier circuit 2 is connected via a connection 12' to the electrically conductive layer 13.

Figure 7:
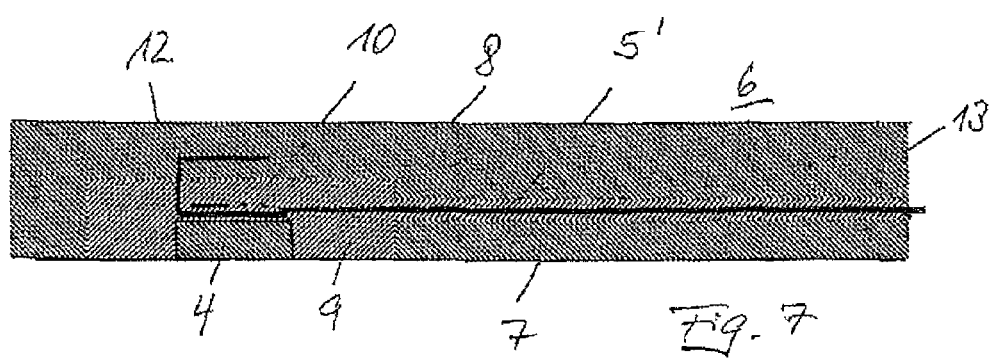
FIG. 7 shows a variant of the arrangement according to FIG. 6, in which the nonconductive material of the wall separates a conductive outer layer from a conductive inner layer of the wall.

The variant represented in FIG. 7 shows a wall 6 of the liner, which is formed predominantly by a conductive layer 13 so that the outer side 8 is formed fully, and the inner face 7 predominantly, by the conductive layer. The nonconductive material 9 surrounds the electrically conductive section 4 on all sides—with the exception of the inner face 7—as well as the amplifier circuit 10 arranged thereon and the conductor 5'.

Figure 8:
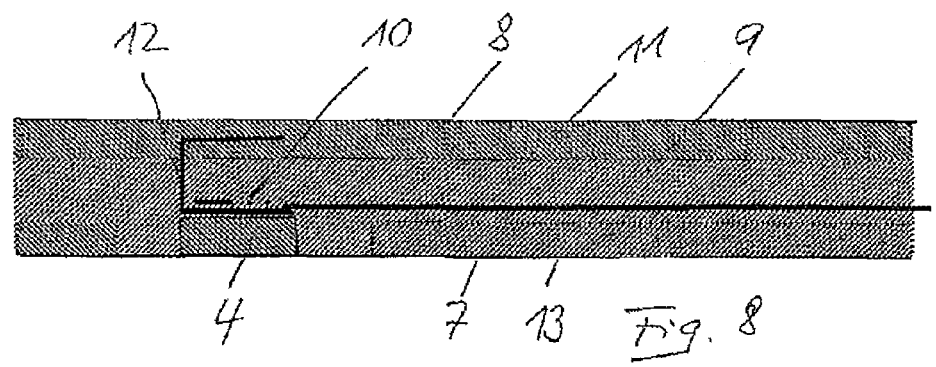
FIG. 8 shows a schematic electrical amplifier circuit having an input terminal connected to the electrically conductive section, an output terminal and two terminals for a voltage supply.

In the variant represented in FIG. 8, the wall 6 consists of a conductive layer 11 on the outer side 8, an electrically conductive layer 3 on the inner face 7 and an interlayer of the nonconductive material 9, applied between the two electrically conductive layers, surrounds—as represented—the electrically conductive section 4 with the amplifier circuit 10 arranged thereon on all sides—with the exception of the inner face 7.

Figure 9:
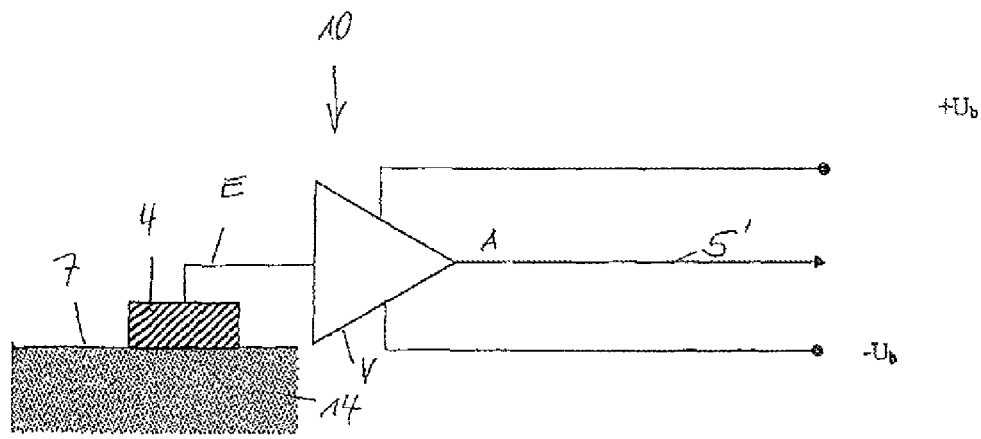
FIG. 9 shows a representation according to FIG. 8 for a field-effect transistor.
Figure 10:
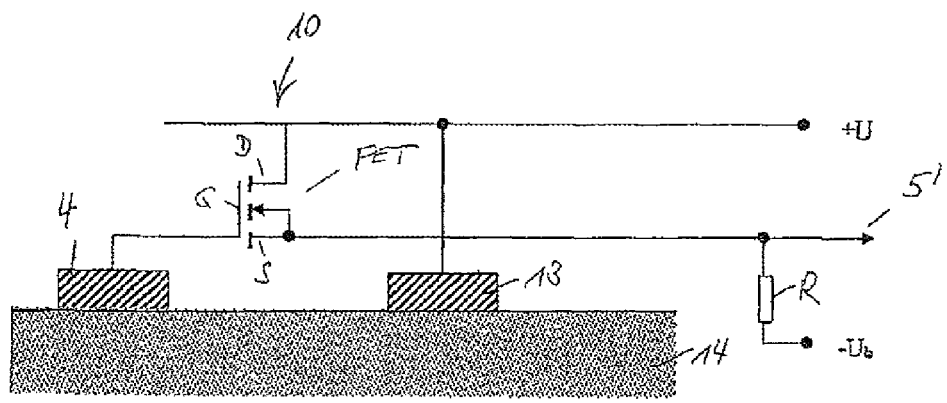
FIG. 10 shows a representation according to FIG. 9 for a circuit variant in which a potential of the supply voltage is delivered via an electrically conductive layer of the wall.
Figure 11:
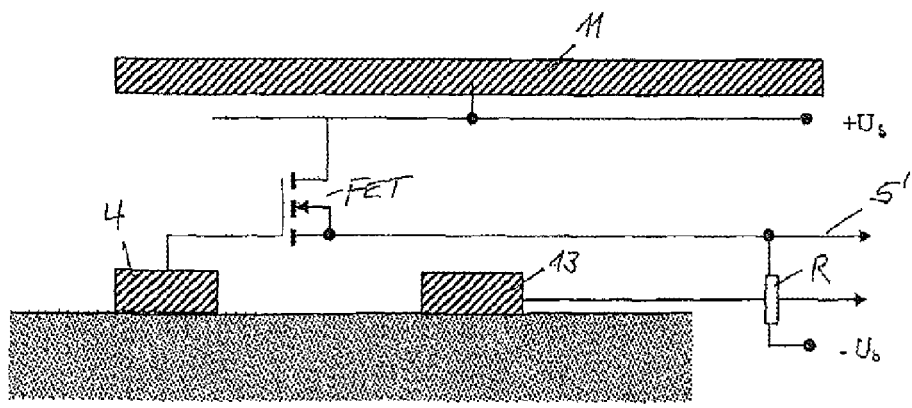
FIG. 11 shows a schematic section through a wall of a liner having an electrically conductive section which is formed integrally with an electrical conductor.

It is therefore clear that the nonconductive material 9 of the wall in any event covers the electrically conductive section 4 on all sides so that the latter remains uncovered only toward the inner face 7. Furthermore, the nonconductive material 9 surrounds the conductors 5, 5' on all sides, in order to ensure a reliable signal line. The nonconductive material preferably forms a layer extending over the entire wall 6 of the liner, although it may also be formed only locally within the wall 6 of the liner 1, as illustrated in FIG. 7. FIGS. 9 to 11 schematically represent possible electrical circuit configurations for the amplifier circuit 10.

FIG. 9 schematically shows the electrically conductive section 4, which bears with its surface on the inner face 7 on the skin 14 of an amputation stump and picks up electrical signals transmitted via the skin 14. The electrical signal passes via a connection of the amplifier circuit 10 to a first terminal E of an amplifier V of the amplifier circuit 10. The amplified signal passes via a terminal A onto the conductor 5, in order to be delivered as an amplified signal. The amplifier V is furthermore connected to supply lines $+U_b$ and $-U_b$, via which the operating voltage for the amplifier V is supplied. FIG. 10 therefore shows a monopolar amplifier module with a voltage supply.

FIG. 10 shows an amplifier circuit 10, which is formed by a field-effect transistor FET. The latter is connected by a terminal D to the supply line $+U_b$ and by a terminal S via a resistor R to the supply line $-U_b$. A further terminal G is connected directly to the electrically conductive section 4, so that electrical measurement signals from the skin 14 are delivered to this terminal G via the electrically conductive section 4. The field-effect transistor FET is in this case connected as a source follower circuit, in which current amplification takes place rather than voltage amplification. It acts as an impedance converter and leads to a low output impedance. The point of connection between the terminal S and the resistor R forms the output of the amplifier circuit 10, and is connected to the conductor 5'.

FIG. 10 also illustrates that one pole of the supply voltage ($+U_b$) is connected to the electrically conductive layer 13, which appears on the skin 14, so that the circuit represented in FIG. 10 can be implemented with the embodiments represented in FIGS. 6 and 7.

The circuit represented in FIG. 11 likewise again constitutes a source follower circuit of an FET, which can be implemented with the exemplary embodiment according to FIG. 8, i.e. with an electrically conductive layer 11 on the outer side of the wall 6 and an electrically conductive layer 13 on the inner face 7. The electrically conductive layer 13 on the inner face 7 may in this case be connected to its own pole, for example a neutral or ground conductor.

Since the resistor R for implementing the source follower circuit can be implemented outside the liner 1, for example in the plug appendage 2, no additional wiring outlay occurs in the circuit configurations according to FIGS. 10 and 11 also, since only a conductor 5' inside the liner is required in order to deliver the amplified measurement signal.

The invention claimed is:

1. A liner configured for use between a body part and an inner surface of a prosthetic socket, the liner comprising:
   a tubular shaped wall having a closed distal end and a side wall, the tubular shaped wall configured to tightly enclose the body part on an exterior of a wearer, the wall comprising an electrically nonconductive material and a shape which is adapted to the body part or adapts thereto by virtue of an elasticity of the tubular shaped wall;

wherein the tubular shaped wall is configured to bear on a skin surface of the body part via an inner face, and the inner face is provided with at least one electrically conductive section, the at least one electrically conductive section being arranged on the side wall to transmit electrical signals from or to the skin of the body part through the electrically nonconductive material;

wherein the at least one electrically conductive section is integrated into and surrounded by the electrically nonconductive material except along the inner face and is connected to at least one conductor, the at least one conductor passing internal the electrically nonconductive material from the at least one electrically conductive section to the closed distal end;

an amplifier circuit which is covered by the nonconductive material of the tubular shaped wall is connected by at least one terminal of the amplifier circuit to the conductive section, and is arranged directly on the conductive section, and at least one other terminal of the amplifier circuit is connected to the at least one conductor;

a surface-wide electrically conductive layer positioned on an outer surface of the tubular shaped wall opposite the electrically conductive section and the at least one conductor, the outer surface being arranged opposite the inner face, the surface-wide electrically conductive layer is arranged to guard the electrically conductive section and the at least one conductor against interference signals.

2. The liner as claimed in claim 1, wherein the at least one conductor is formed integrally with the at least one electrically conductive section.

3. The liner as claimed in claim 1, wherein the at least one electrically conductive section is connected to a separate conductor laid in the nonconductive material.

4. The liner as claimed in claim 1, wherein the at least one conductor comprises metal.

5. The liner as claimed in claim 1, wherein the surface-wide electrically conductive layer is formed so that the surface-wide electrically conductive layer can be connected to a terminal of an electricity supply.

6. The liner as claimed in claim 5, wherein the surface-wide electrically conductive layer is arranged for connection to a ground potential of the electricity supply.

7. The liner as claimed in claim 1, wherein the amplifier circuit has at least one transistor.

8. The liner as claimed in claim 7, wherein the amplifier circuit is formed by a field-effect transistor (FET) with its terminals.

9. The liner as claimed in claim 7, wherein the at least one transistor is a field-effect transistor (FET).

10. The liner as claimed claim 1, wherein the nonconductive material of the tubular shaped wall is a hydrophobic material.

11. The liner as claimed in claim 1, wherein the at least one electrically conductive section consists of a hydrophilic material.

12. The liner as claimed in claim 1, wherein the surface-wide electrically conductive layer is positioned on the outer surface along at least the side wall and closed distal end.

13. The liner as claimed in claim 1, wherein the surface-wide electrically conductive layer is positioned on the outer surface from at least the at least one electrically conductive section to the closed distal end.

14. The liner as claimed in claim 1, wherein the surface-wide electrically conductive layer is electrically insulated from the at least one electrically conductive section and the at least one conductor.

15. A liner configured for use between a body part and an inner surface of a prosthetic socket, the liner comprising:
 a tubular shaped wall configured to tightly enclose the body part on an exterior of a wearer, the tubular shaped wall comprising:
  a closed distal end;
  a side wall;
  an electrically nonconductive material;
  at least one conductor extending internal the electrically nonconductive material to the closed distal end;
  an inner face arranged to contact a skin surface of the body part;
  an outer surface arranged opposite the inner face;
  an electrically conductive section integrated into and surrounded by the electrically nonconductive material except along the inner face at the side wall, the electrically conductive section being connected to the at least one conductor;
  a wall shape which adapts to a shape of the body part by an elastic property of the tubular shaped wall;
  a surface-wide electrically conductive material positioned on the outer surface opposite the electrically conductive section and the at least one conductor, the surface-wide electrically conductive layer being insulated from the electrically conductive section and the at least one conductor and arranged to guard the electrically conductive section and the at least one conductor against interference signals;
  wherein the electrically conductive section is configured to transmit electrical signals from or to the skin of the body part through the electrically nonconductive material of the tubular shaped wall;
 a plug appendage at the closed distal end of the tubular shaped wall, wherein at least one of the electrically conductive section and the at least one conductor extends within the electrically non-conductive material to the plug appendage at the closed distal end.

16. The liner as claimed in claim 15, wherein the at least one conductor is formed integrally with the electrically conductive section.

17. The liner as claimed in claim 15, wherein the electrically conductive section is connected to a second conductor that is separate from the at least one conductor and positioned in the nonconductive material.

18. The liner as claimed in claim 17, wherein the second conductor comprises metal.

19. The liner as claimed in claim 15, wherein the tubular shaped wall further comprises an amplifier circuit which is covered by the nonconductive material of the tubular shaped wall, is connected by at least one terminal to the electrically conductive section, and is arranged directly on the electrically conductive section, and at least one other terminal of the amplifier circuit is connected to the at least one conductor.

20. The liner as claimed in claim 19, wherein surface-wide electrically conductive layer is formed so that it can be connected to a terminal of an electricity supply.

21. The liner as claimed in claim 20, wherein the surface-wide electrically conductive layer is arranged for connection to a ground potential of the electricity supply.

22. A device configured for use between a body part and an inner surface of a prosthetic socket, the device comprising:
a tubular shaped wall having a closed distal end, an inner face, an outer surface, and a side wall, the outer surface being arranged opposite the inner face, the tubular shaped wall configured to tightly enclose the body part on an exterior of a wearer, comprising an electrically nonconductive material and a shape which is adapted to the body part or adapts thereto by virtue of an elasticity of the tubular shaped wall;
wherein the tubular shaped wall is configured to bear on a skin surface of the body part via the inner face, and the inner face is provided with at least one electrically conductive section positioned on the side wall, the at least one electrically conductive section being arranged to transmit electrical signals from or to the skin of the body part through the electrically nonconductive material;
wherein the electrically conductive section is integrated into and surrounded by the electrically nonconductive material except along the inner face and is connected to at least one conductor passing through the electrically nonconductive material to the closed distal end;
wherein the conductive section is integrated into the nonconductive material of the tubular shaped wall and forms a unitary and continuously formed inner face with the nonconductive material of the tubular shaped wall;
wherein the tubular shaped wall includes a surface-wide electrically conductive layer positioned on the outer surface opposite the electrically conductive section and the at least one conductor, the surface-wide electrically conductive layer being insulated from the electrically conductive section and the at least one conductor and arranged to guard the electrically conductive section and the at least one conductor against interference signals.

23. A liner configured for use between a body part and an inner surface of a prosthetic socket, the liner comprising:
a tubular shaped wall having a closed distal end, an inner face, an outer surface, and a side wall, the outer surface being arranged opposite the inner face, the tubular shaped wall configured to tightly enclose the body part on an exterior of a wearer, the tubular shaped wall comprising an electrically nonconductive material and a shape which is adapted to the body part or adapts thereto by virtue of an elasticity of the tubular shaped wall;
wherein the tubular shaped wall is configured to bear on a skin surface of the body part via the inner face, and the inner face is provided with at least one electrically conductive section positioned on the side wall, the at least one electrically conductive section being arranged to transmit electrical signals from or to the skin of the body part through the electrically nonconductive material;
wherein the electrically conductive section is integrated into and surrounded by the electrically nonconductive material except along the inner face and is connected to at least one conductor passing through the electrically nonconductive material to the closed distal end;
wherein at least one of the electrically conductive section and the at least one conductor extends within the electrically non-conductive material to the closed distal end;
wherein the tubular shaped wall includes a surface-wide electrically conductive layer positioned on the outer surface opposite the electrically conductive section and the at least one conductor, the surface-wide electrically conductive layer being insulated from the electrically conductive section and the at least one conductor and arranged to guard the electrically conductive section and the at least one conductor against interference signals.

24. A liner configured for use between a body part and an inner surface of a prosthetic socket, the liner comprising:
a tubular shaped wall having a closed distal end, an inner face, an outer surface, and a side wall, the outer surface being arranged opposite the inner face, the tubular shaped wall configured to tightly enclose the body part on an exterior of a wearer, the tubular shaped wall comprising an electrically nonconductive material and a shape which is adapted to the body part or adapts thereto by virtue of an elasticity of the tubular shaped wall;
wherein the tubular shaped wall is configured to bear on a skin surface of the body part via the inner face, and the inner face is provided with at least one electrically conductive section positioned on the side wall, the at least one electrically conductive section being formed integrally inside the electrically non-conductive material and being arranged to transmit electrical signals from or to the skin of the body part through the electrically nonconductive material;
wherein the electrically conductive section is integrated into and surrounded by the electrically nonconductive material except along the inner face and is connected to at least one conductor passing through the electrically nonconductive material to a plug appendage at the closed distal end;
wherein the tubular shaped wall includes a surface-wide electrically conductive layer positioned on the outer surface opposite the electrically conductive section and the at least one conductor, the surface-wide electrically conductive layer being insulated from the electrically conductive section and the at least one conductor and arranged to guard the electrically conductive section and the at least one conductor against interference signals.

25. A liner configured for use between a body part and an inner surface of a prosthetic socket, the liner comprising:
a tubular shaped wall having a closed distal end, an inner face, an outer surface, and a side wall, the outer surface being arranged opposite the inner face, the tubular shaped wall configured to tightly enclose the body part on an exterior of a wearer, the tubular shaped wall comprising an electrically nonconductive material, the inner face comprising at least one electrically conductive section;
wherein the tubular shaped wall is configured to be positioned on the body part and adapt to a shape of the body part, and the inner face of the tubular shaped wall is configured to bear on a skin surface of the body part, the at least one conductive section being arranged on the side wall to transmit electrical signals from or to the skin surface of the body part through the electrically nonconductive material;
wherein the electrically conductive section is integrated into and surrounded by the electrically nonconductive material except along the inner face and is connected to at least one conductor, the at least one conductor passing through the electrically nonconductive material to the closed distal end;

wherein at least one of the electrically conductive section and the at least one conductor extend within the electrically non-conductive material and are electrically connected to a plug appendage at the closed distal end;

wherein the tubular shaped wall includes a surface-wide electrically conductive layer positioned on the outer surface opposite the electrically conductive section and the at least one conductor, the surface-wide electrically conductive layer being insulated from the electrically conductive section and the at least one conductor and arranged to guard the electrically conductive section and the at least one conductor against interference signals.

26. A liner configured for use between a body part and an inner surface of a prosthetic socket, the liner comprising:

a tubular shaped wall having a closed distal end, the tubular shaped wall configured to tightly enclose the body part on an exterior of a wearer, the tubular shaped wall comprising an electrically nonconductive material, an outer surface, at least one conductor passing internal the electrically nonconductive material to the closed distal end, and an inner face, the outer surface being arranged opposite the inner face, the outer surface comprising a surface-wide electrically conductive layer, the inner face comprising at least one electrically conductive section, the surface-wide electrically conductive layer arranged opposite the electrically conductive section and the at least one conductor;

wherein the tubular shaped wall is configured to be positioned on the body part and adapt to a shape of the body part, and the inner face of the tubular shaped wall is configured to bear on a skin surface of the body part, the at least one conductor is connected to the at least one electrically conductive section, the at least one conductor and the at least one electrically conductive section being arranged to transmit electrical signals from or to the skin surface of the body part through the tubular shaped wall;

wherein the at least one conductor extends within the electrically nonconductive material to the closed distal end;

wherein the surface-wide electrically conductive layer being insulated from the electrically conductive section and the at least one conductor and arranged to guard the electrically conductive section and the at least one conductor against interference signals.

* * * * *